(12) United States Patent
Church et al.

(10) Patent No.: US 10,910,085 B2
(45) Date of Patent: Feb. 2, 2021

(54) METHODS OF MAKING POLYPEPTIDES WITH NON-STANDARD AMINO ACIDS USING GENOMICALLY RECODED ORGANISMS

(71) Applicant: President and Fellows of Harvard College, Cambridge, MA (US)

(72) Inventors: George M. Church, Brookline, MA (US); Christopher J. Gregg, Roslindale, MA (US); Marc J. Lajoie, Cambridge, MA (US); Daniel J. Mandell, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/522,569

(22) PCT Filed: Oct. 28, 2015

(86) PCT No.: PCT/US2015/057780
§ 371 (c)(1),
(2) Date: Apr. 27, 2017

(87) PCT Pub. No.: WO2016/069726
PCT Pub. Date: May 6, 2016

(65) Prior Publication Data
US 2017/0337323 A1    Nov. 23, 2017

Related U.S. Application Data

(60) Provisional application No. 62/069,484, filed on Oct. 28, 2014.

(51) Int. Cl.
*G16B 15/00* (2019.01)
*C12Q 1/37* (2006.01)
*C12N 15/52* (2006.01)
*C12N 15/10* (2006.01)

(52) U.S. Cl.
CPC ........... *G16B 15/00* (2019.02); *C12N 15/102* (2013.01); *C12N 15/1058* (2013.01); *C12Q 1/37* (2013.01); *C07K 2319/00* (2013.01); *C12N 15/52* (2013.01)

(58) Field of Classification Search
None
See application file for complete search history.

(56) References Cited

U.S. PATENT DOCUMENTS

| | | | |
|---|---|---|---|
| 2006/0194256 A1 | 8/2006 | Miao et al. | |
| 2010/0273978 A1* | 10/2010 | McCraith | C07K 14/505 530/322 |
| 2014/0154744 A1 | 6/2014 | Soll et al. | |

* cited by examiner

*Primary Examiner* — Channing S Mahatan
(74) *Attorney, Agent, or Firm* — Banner & Witcoff, Ltd.

(57) ABSTRACT

A method of making a polypeptide including at least one covalent bond between a pair of reactive side chains of corresponding amino acids, wherein the covalent bond is insensitive to reduction is provided including genetically modifying a genomically recoded organism to express a corresponding synthetase, tRNA or synthetase/tRNA pair for translating mRNA encoding the corresponding amino acids having the reactive side chains into the polypeptide and to express the polypeptide including the at least one pair of the reactive side chains wherein the reactive side chains are oriented near one another when the expressed polypeptide is in a folded configuration, wherein the reactive side chains react to form the covalent bond that is insensitive to reduction.

11 Claims, 11 Drawing Sheets

METHODS OF MAKING POLYPEPTIDES WITH NON-STANDARD AMINO ACIDS USING GENOMICALLY RECODED ORGANISMS

RELATED APPLICATION DATA

This application is a National Stage Application under 35 U.S.C. 371 of PCT application PCT/US15/57780 designating the United States and filed Oct. 28, 2015; which claims the benefit of U.S. provisional application No. 62/069,484 and filed Oct. 28, 2014 each of which are hereby incorporated by reference in their entireties.

STATEMENT OF GOVERNMENT INTERESTS

This invention was made with government support under DE-FG02-02ER63445 awarded by Department of Energy. The government has certain rights in the invention.

FIELD

The present invention relates in general to methods of making polypeptides with non-standard amino acids using genomically recoded organisms.

BACKGROUND

Naturally-occurring (standard) amino acids are the 20 unique building blocks composing all proteins derived from biological systems. Synthetic amino acids can be designed to bear functional groups beyond those encoded by the 20 amino acids. To date, more than 70 non-standard amino acids (NSAAs) have been developed for in vivo protein translation. See Liu et al., *Annual Review of Biochemistry* 79:413-444 (2010). However, a need exists for methods of designing proteins with non-standard amino acids.

SUMMARY

Embodiments of the present disclosure are directed to methods of making a polypeptide including at least one pair of nonstandard amino acids with catalytically reactive side chains including genetically modifying a genomically recoded organism to express the polypeptide including at least one pair of nonstandard amino acids wherein the at least one pair of nonstandard amino acids are oriented near one another when the expressed polypeptide is in a folded configuration, and wherein the at least one pair of nonstandard amino acids react to form a covalent bond. According to one aspect, the covalent bond is an oxidation-reduction insensitive covalent bond. According to one aspect, the covalent bond is formed in the absence of a catalyst separate from the polypeptide itself, as the polypeptide folding activity serves as a catalyst for the covalent bonding. Accordingly, aspects of the method do not use a separate catalyst or an exogenous catalyst. According to one aspect, the polypeptide further includes modified, substituted or optimized amino acids which maintain the backbone orientation of the polypeptide when the at least one pair of nonstandard amino acids react to form a covalent bond in the absence of a catalyst. According to one aspect, the at least one pair of nonstandard amino acids in a free form within the genomically recoded organism are unreactive in the absence of a catalyst. According to one aspect, the at least one pair of nonstandard amino acids includes a side chain pair selected from the group consisting of azido/aliphatic alkyne, azido/strained alkyne, ketone/amine, aldehyde/amine, ketone/hydrazide, ketone/aminooxy, aldehyde/hydrazide, aldehyde/aminooxy, and boronate/vicinal diol. According to one aspect, the genomically recoded organism has been genetically modified to express a corresponding synthetase/tRNA pair for translating mRNA encoding the non-standard amino acid into the polypeptide. According to one aspect, the genomically recoded organism is a bacterium. According to one aspect, the genomically recoded organism is *E. coli*.

Aspects of the present disclosure are also directed to a method of in silico polypeptide design including identifying a three-dimensional folded structure of a target polypeptide in a native environment, analyzing the three-dimensional folded structure to identify target amino acid pair positions and/or geometries to accommodate a pair of nonstandard amino acids in a bonded state while substantially maintaining the three-dimensional folded structure of the target polypeptide in a native environment, substituting in silico the target amino acid pair with the pair of nonstandard amino acids to create a modified target polypeptide, determining a difference in structure between the three-dimensional folded structure of the target polypeptide and a three-dimensional folded structure of the modified target polypeptide, and substituting or altering in silico neighboring native amino acids with substitute standard amino acids to reduce the difference between the structure of the three-dimensional folded structure of the target polypeptide and the structure of the three-dimensional folded structure of the modified target polypeptide.

According to another aspect, a method is provided for in silico polypeptide design including the steps of computer modeling of a three-dimensional folded structure of a target polypeptide wherein the target polypeptide has an activity, analyzing the three-dimensional folded structure to identify pairs of native amino acids whose positions in the structure are candidates to accommodate the geometries of a reactive, nonstandard amino acid pair in a bonded state, substituting in silico the native amino acid pair with the pair of nonstandard amino acids to create a modified target polypeptide, bonding in silico the pair of nonstandard amino acids, and substituting in silico neighboring native amino acids with other different native amino acids or altering neighboring native amino acids to create a three-dimensional folded structure of the modified target polypeptide which is substantially similar to the three-dimensional folded structure of the target polypeptide such that the modified target polypeptide has an activity substantially similar to the target polypeptide.

According to another aspect, a method is provided for in silico polypeptide design including the steps of computer modeling of a three-dimensional folded structure of a target polypeptide with a native composition, analyzing the three-dimensional folded structure to identify pairs of native amino acids whose positions in the structure can accommodate a reactive, nonstandard amino acid pair in a bonded state, while substantially maintaining the three-dimensional folded structure of the target polypeptide as with the native composition, substituting in silico the native amino acid pair with the pair of nonstandard amino acids to create a modified target polypeptide, determining a difference between the three-dimensional folded structure of the target polypeptide and a three-dimensional folded structure of the modified target polypeptide, and substituting or altering in silico neighboring native amino acids with other amino acids or other native amino acid conformations to reduce the difference between the three-dimensional folded structure of the target polypeptide and the three-dimensional folded structure of the modified target polypeptide.

BRIEF DESCRIPTION OF THE DRAWINGS

The foregoing and other features and advantages of the present invention will be more fully understood from the following detailed description of illustrative embodiments taken in conjunction with the accompanying drawings in which.

DETAILED DESCRIPTION OF CERTAIN PREFERRED EMBODIMENTS

Figure 1A:
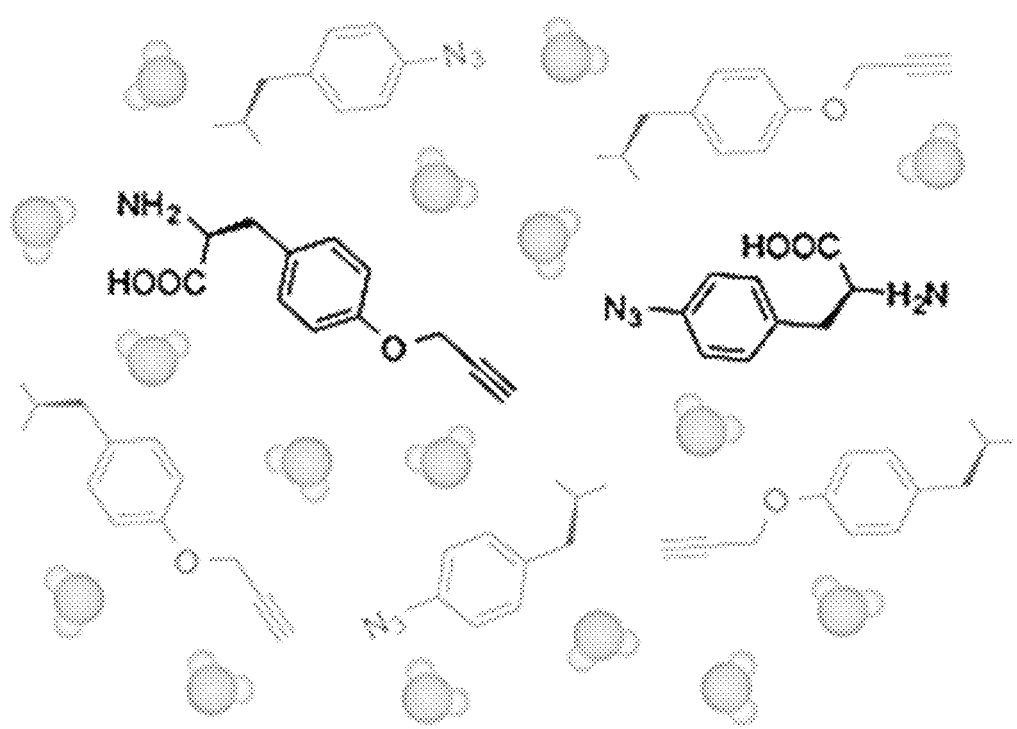
FIG. 1 is a schematic illustration of a method of identifying reactable amino acids and placing them within the structure of a folded protein.

The present invention is directed to methods of making polypeptides including a pair of non-standard amino acids having functional groups that bind together when the polypeptide folds under certain environmental conditions, such as in vivo conditions. According to one aspect, a genomically recoded organism expresses the polypeptide including a pair of non-standard amino acids having functional groups that bind together. According to one aspect, the functional groups of the pair of non-standard amino acids are non-reactive as free-form or single amino acids, such as when present in an in vivo environment, such as a cell. Since they are non-reactive, the pair of non-standard amino acids are non-toxic to the cell within which they are present, for example as free floating species. The non-standard amino acids of the pair are highly specific for each other with respect to bonding.

Upon folding of the polypeptide under certain environmental conditions, the binding of the functional groups of the pair of non-standard amino acids within the polypeptide is catalyzed by protein folding or protein interactions. It is understood in the current disclosure that "protein" may refer to a full length protein, a protein complex, a protein subunit or domain, or a polypeptide with a determined structure. According to one aspect, the binding of the functional groups of the pair of non-standard amino acids within the polypeptide occurs in the absence of an exogenous catalyst. It is to be understood that the polypeptide folding acts to catalyze the covalent bonding of the functional groups and that a separate or exogenous catalyst is not needed. According to one aspect, the bond formed between the functional groups of the pair of non-standard amino acids within the polypeptide is a covalent bond. According to one aspect, the bond formed between the functional groups of the pair of non-standard amino acids within the polypeptide is a covalent bond which is insensitive to oxidation or reduction. According to one aspect, the bond formed between the functional groups of the pair of non-standard amino acids within the polypeptide is a covalent bond which is irreversible under the certain environmental conditions. Although, certain aspects of the present disclosure envision the use of orthogonally reversible bonds where protein folding catalyzes bond formation and protein unfolding or other three dimensional change in the protein or other stimulus causes the bond to break. According to one aspect, the functional groups, also referred to as side chains, of the non-standard amino acids within the polypeptide react or bind together within the folded polypeptide microenvironment. No separate catalyst is required to catalyze the covalent bonding of the functional groups of the non-standard amino acid pair.

According to one aspect, the methods described herein are useful for protein engineering. A known protein having known utility or function when in a particular three-dimensional configuration under certain environmental conditions can be stabilized insofar as covalent binding between non-standard amino acids can be used to stabilize the active three-dimensional configuration when the protein is placed in environmental conditions which do not favor the active three-dimensional configuration. The covalent binding between the two non-standard amino acids of the pair effectively stabilizes the active three-dimensional configuration by holding the active three-dimensional configuration in place. In this manner, the active three-dimensional configuration of the protein may be stabilized under a variety of environmental conditions including conditions considered harsh and destabilizing for the particular protein.

Aspects of the present disclosure relate to the in silico design of polypeptides having non-standard amino acid binding pairs at locations where the non-standard amino acids will bind when the protein is folded under certain conditions. According to one aspect, a known protein having a known three-dimensional active conformation is analyzed to identify amino acid sites where a pair of natural amino acids can be replaced with a pair of non-standard amino acids having functional groups which bind together under protein folding. According to this aspect, computational tools are used to engineer proteins that drive their own covalent bond formation between non-standard amino acid pairs during protein folding. According to one aspect, a geometric matching algorithm is used to scan the structure of a protein to identify amino acid positions accommodating the geometry of a particular non-standard amino acid in the bound state. Geometric matching algorithms are known to those of skill in the art. In another embodiment, amino acid positions suitable to accommodate the pair of particular non-standard amino acids in the bound state is determined by protein design simulations, which may utilize Monte Carlo sampling or dead-end elimination. Protein design techniques including Monte Carlo sampling and dead-end elimination are known to those of skill in the art (see Kuhlman, B. & Baker, D. Native protein sequences are close to optimal for their structures. Proc Natl Acad Sci USA 97, 10383-10388 (2000) and Desmet et al. The dead-end elimination theorem and its use in protein side-chain positioning. Nature 356:6369 (1992) hereby incorporated by reference in their entirety.

The protein is then altered in silico to replace the natural amino acid pair at amenable positions in the folded polypeptide with the non-standard amino acid pair and the geometry of the modified protein is analyzed to determine whether the functional groups of the non-standard amino acid pair are within a reaction distance and orientation such that the functional groups are close enough together and properly oriented to react when the protein is in a folded configuration. According to one aspect, the modified protein maintains an active three-dimensional structure when the non-standard amino acid pair are bound together.

According to an additional aspect, the ability of the functional groups of the non-standard amino acid pair to bind together is optimized by analyzing the chemistry and/or geometry of one or more natural amino acids of the protein and determining whether replacing the one or more natural amino acids with one or more different amino acids will optimize the reaction distance and orientation between the functional groups of the non-standard amino acids thereby promoting reaction of the functional groups of the non-standard amino acids. In this manner, in silico modifications of the modified protein are made such that the three-dimensional structure of the modified protein is substantially similar to the unmodified protein. According to an additional aspect, the ability of the functional groups of the non-standard amino acid pair to bind together is optimized by analyzing the chemistry and/or the geometry of one or more natural amino acids of the protein and determining whether altering the structure of the one or more natural amino acids with a different structure will optimize the reaction distance and orientation between the functional groups of the non-standard amino acids thereby promoting reaction of the functional groups of the non-standard amino acids. In this manner, in silico modifications of the modified protein are made such that the three-dimensional structure of the modified protein is substantially similar to the unmodified protein.

According to an additional aspect, the three-dimensional structure of the unmodified protein is optimized in the modified protein by analyzing the chemistry and/or the geometry of one or more natural amino acids of the protein and determining whether replacing the one or more natural amino acids with one or more different amino acids will maintain an active conformation of the three-dimensional structure of the unmodified protein. In this manner, in silico modifications of the modified protein are made such that the three-dimensional structure of the modified protein is substantially similar to the unmodified protein. According to an additional aspect, the three-dimensional structure of the unmodified protein is optimized in the modified protein by analyzing the chemistry and/or geometry of one or more natural amino acids of the protein and determining whether altering the structure of the one or more natural amino acids will maintain an active conformation of the three-dimensional geometry of the unmodified protein. In this manner, in silico modifications of the modified protein are made such that the three-dimensional structure of the modified protein is substantially similar to the unmodified protein.

Accordingly, an in silico method is described herein for determining a pair of amino acid sites within a protein that can be substituted for a pair of non-standard amino acids which covalently bind together. Neighboring amino acids can then be replaced or altered to maintain the bound non-standard amino acids while minimally altering or changing the global structure of the protein.

Figure 1B:
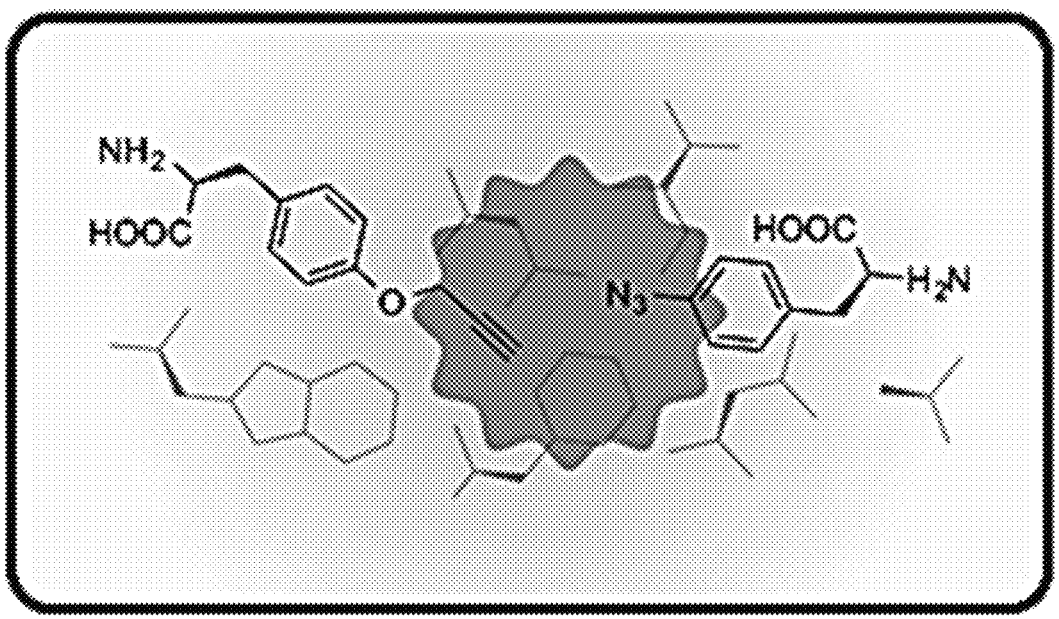
Figure 1C:
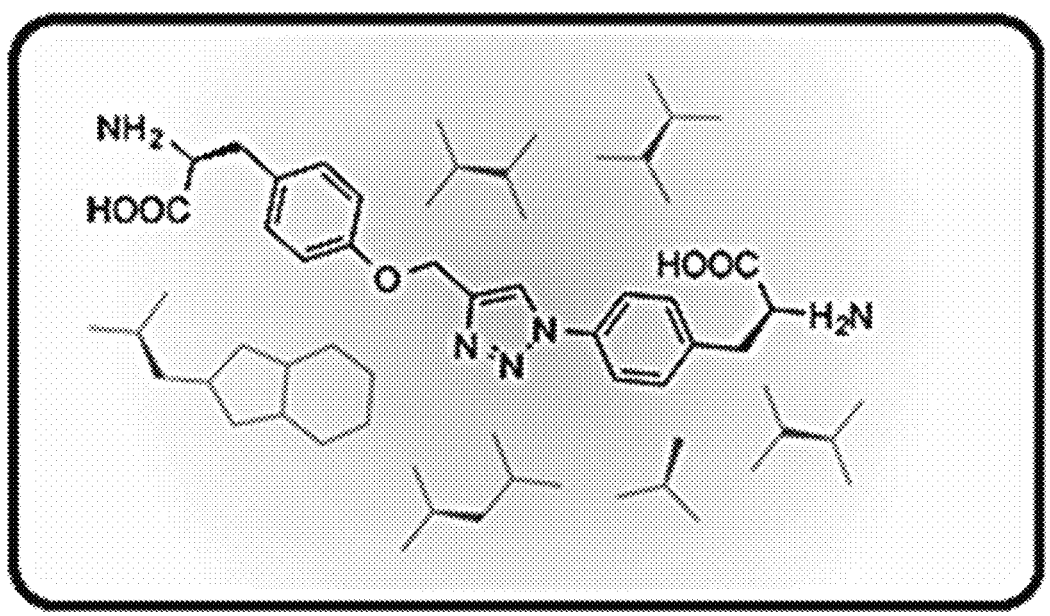

FIG. 1A, FIG. 1B and FIG. 1C are directed to the design of redox-insensitive covalent bonds by in silico design of non-standard amino acids in genomically recoded organisms. FIG. 1A depicts an exemplary pair of nonstandard amino acids having functional groups that react when oriented to interact with each other within a folded protein. The bio-orthogonal, reactable amino acids diffuse freely in the cytosol in the absence of a catalyst. The non-standard amino acids capable of covalent bond formation (dark sticks) are selected to have low reactivity as free amino acids so they remain inert in solution and non-toxic within a cell. As illustrated in FIG. 1B, a database of protein structures is computationally scanned for polypeptide backbone conformations that can accommodate the non-standard amino acids as a covalent adduct. Modifying the wild-type protein or protein complex to replace a pair of natural amino acids with the pair of non-standard amino acids may result in unfavorable steric or electrostatic interactions with neighboring chemical moieties, i.e., steric clashes (star area) with neighboring sidechains (faint sticks) may result that prevent non-standard amino acid functional group bond formation and protein folding. As illustrated in FIG. 1C, the method includes computationally redesigning the neighboring sidechains to create a protein microenvironment that both accommodates the bonded non-standard amino acid sidechains and catalyzes non-standard amino acid bond formation by stabilizing the transition state using the free energy of protein folding or association.

Figure 2:
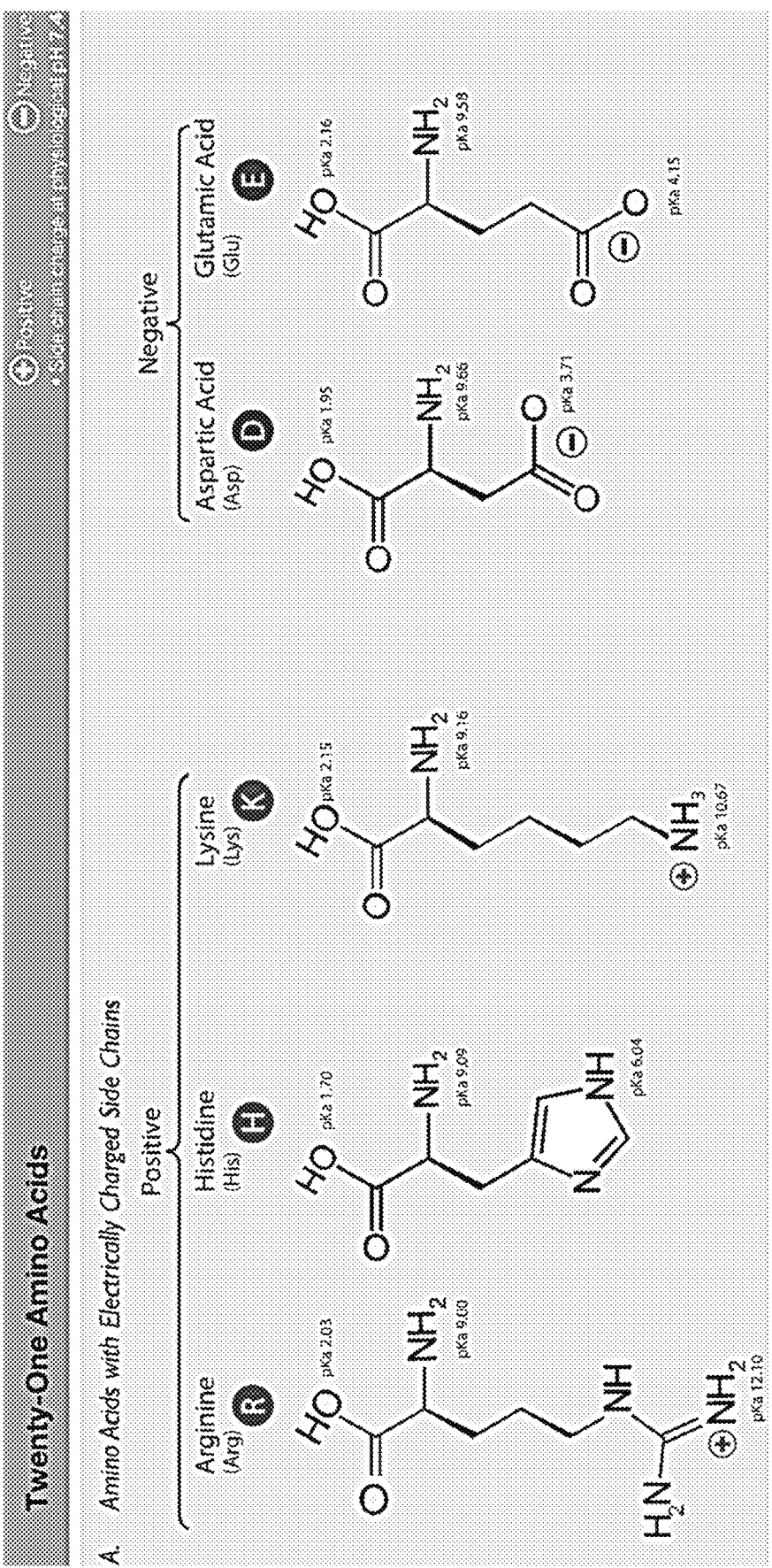
FIG. 2 shows the structure of natural amino acids.
Figure 2:
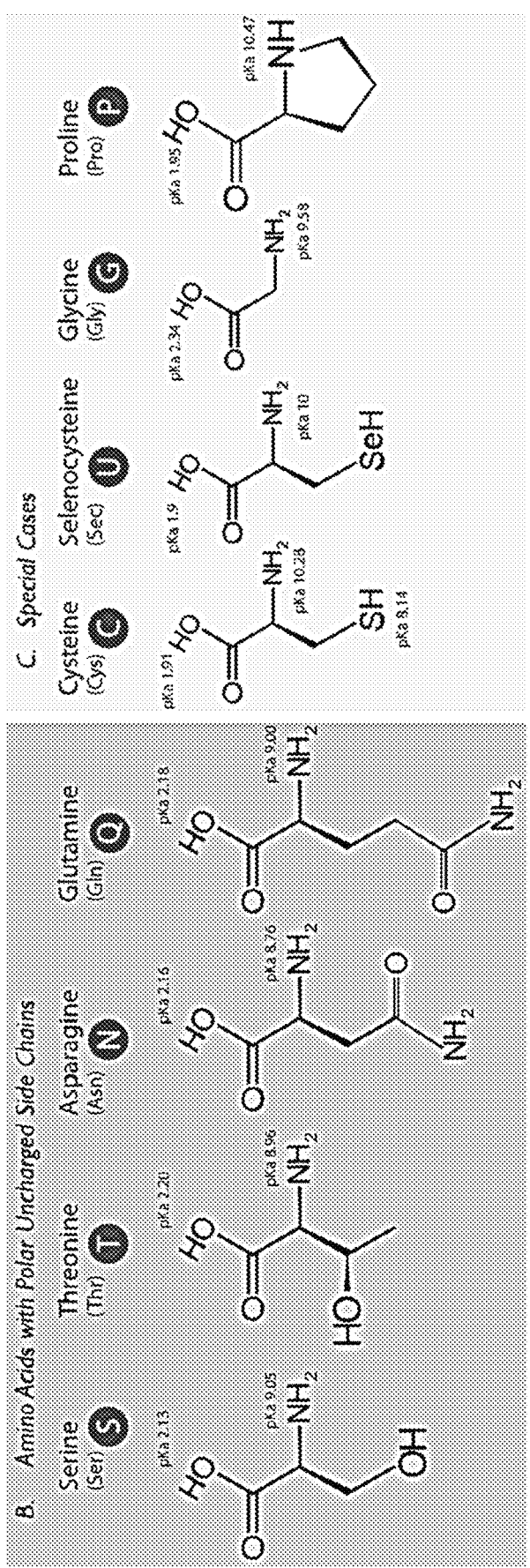
Figure 2:
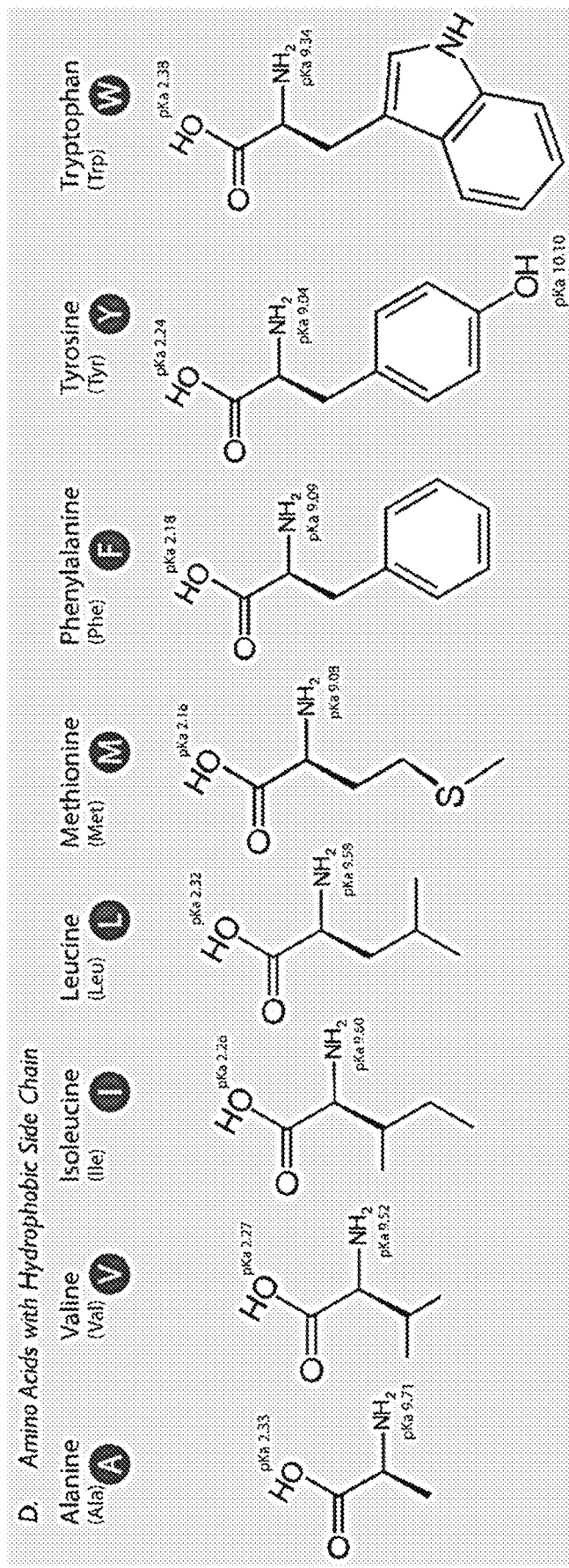

Standard amino acids within the scope of the present disclosure include the naturally occurring amino acids Glycine, Alanine, Valine, Leucine, Isoleucine, Serine, Cysteine, Selenocysteine, Threonine, Methionine, Proline and its derivatives, Phenylalanine, Tyrosine, Tryptophan, Histidine, Lysine and its derivatives, Pyrrolysine, Arginine, Aspartate, Glutamate, Asparagine, and Glutamine the structure of which are shown in FIG. 2.

Non-standard amino acids within the scope of the present disclosure are synthetic amino acids which have been designed to include a non-standard functional group not present in the standard amino acids or are naturally occurring amino acids bearing functional groups not present in the set of standard amino acids. Accordingly, a non-standard amino acid may include the structure of a standard amino acid and which includes a non-standard functional group. A non-standard amino acid may include the basic amino acid portion of a standard amino acid and include a non-standard functional group.

Functional groups include those that can react with each other when placed within the three-dimensional structure of a folded protein. Accordingly, two functional groups may comprise a pair of reactive functional groups. According to one aspect, when the non-standard functional groups are present on a non-standard amino acid, the non-standard amino acid is non-toxic to the cell such as when the non-standard amino acids are freely floating within the cell cytoplasm. The non-standard amino acids which react with one another form covalent bonds. According to one aspect, the covalent bonds are insensitive to oxidation or reduction. According to one aspect, the covalent bonds are irreversible or reversible. According to one aspect, the covalent bonds exhibit low reactivity in the absence of a separate or exogenous catalyst.

The non-standard functional groups described herein can also be referred to as amino acid side chains. Exemplary functional group pairs useful in the methods described herein are (1) azido and aliphatic alkyne, (2) azido and strained alkyne, (3) ketone or aldehyde and amine, (4) ketone or aldehyde and hydrazide or aminooxy, and (5) boronate and vicinal diol.

According to certain aspects of the present disclosure, amino acyl tRNA synthetases are provided to charge tRNAs with the corresponding non-standard amino acids described herein.

According to one particular embodiment, a method is provided for making a polypeptide with a non-standard amino acid pair having functional groups that react to form a covalent bond. It is to be understood that the polypeptide can include more than one non-standard amino acid pair having functional groups that react to form a covalent bond, such as a plurality of non-standard amino acid pairs having functional groups that react to form a covalent bond. The functional groups react as a result of geometric catalysis insofar as no separate catalyst is used for the reaction. Instead, the geometric arrangement of the functional groups as a result of protein folding or association catalyzes the covalent bonding.

According to an exemplary method, candidate non-standard amino acid pairs are identified that can form specific, irreversible covalent bonds with each other in vivo. The toxicity profile of each candidate non-standard amino acid is determined separately in vivo. The toxicity profile of a non-standard amino acid pair is determined in vivo. An orthogonal amino acyl tRNA synthetase is engineered to charge each candidate non-standard amino acid onto tRNAs. The optimal non-standard amino acid concentration for protein production by GFP fluorescence assay is determined. An orthogonal amino acyl tRNA synthetase/tRNA pair for each candidate non-standard amino acid is introduced into the genomically recoded organism, either episomally or chromosomally (e.g., by lambda Red-mediated recombination). A first amino acyl tRNA synthetase/tRNA pair utilizes the first candidate non-standard amino acid of the pair and charges that non-standard amino acid candidate onto a tRNA that recognizes the reassigned UAG codon in the GRO. A second amino acyl tRNA synthetase/tRNA pair utilizes the second candidate non-standard amino acid of the pair and charges that non-standard amino acid candidate onto a tRNA that recognizes a second reassigned triplet codon. Alternatively, both amino acyl tRNA synthetase/tRNA pair may utilize quadruplet codons (UAGA and UAGB) in the genomically recoded organism. An atomic-level model of the covalently bound product between the two candidate non-standard amino acids in an idealized conformation (atomic charges and coordinates quantum mechanically optimized) is created. Using the ideal coordinates, two non-standard amino acid side chains corresponding to the atoms of the reactive side chains in the bound conformation are defined. The optimal conformations ("rotamers") of the free reactive side chains are determined by sampling side chain dihedrals in the context of a dipeptide and the most favorable conformations are stored in a rotamer library. A subset of the bound product is defined to serve as a "reference molecule" for geometric matching (e.g., the triazole ring of the 1,3-dipolar cycloaddition product). Constraints describing the geometric relationship between the reactive side chains and the reference molecule in the idealized (quantum mechanically optimized) bound conformation are encoded. A database of protein structures is searched for scaffolds that can catalyze the reaction by sampling the non-standard amino acid rotamer libraries against all desired positions (may be all positions in all protein structures) to find conformations that satisfy the geometric relationship between the non-standard amino acid and the reference molecule. This can be done by geometric matching (see Zanghellini, A. et al. New algorithms and an in silico benchmark for computational enzyme design. Protein Sci 15, 2785-2794, doi:10.1110/ps.062353106 (2006) hereby incorporated by reference in its entirety) or traditional protein design (see Kuhlman, B. & Baker, D. Native protein sequences are close to optimal for their structures. Proc Natl Acad Sci USA 97, 10383-10388 (2000) hereby incorporated by reference in its entirety. Conformations with backbone clashes can be ignored or relaxed by protein remodeling (see Huang, P. S. et al. RosettaRemodel: a generalized framework for flexible backbone protein design. PLoS One 6, e24109, doi:10.1371/journal.pone.0024109 (2011) hereby incorporated by reference in its entirety. Candidate scaffolds can either be filtered (to remove unfavorable side-chain environments) or redesigned to support the bound product with favorable packing and electrostatic interactions. See Kuhlman, B. & Baker, D. Native protein sequences are close to optimal for their structures. Proc Natl Acad Sci USA 97, 10383-10388 (2000) and Huang, P. S. et al. RosettaRemodel: a generalized framework for flexible backbone protein design. PLoS One 6, e24109, doi:10.1371/journal.pone.0024109 (2011). The redesigned proteins are cloned into an expression plasmid or integrated into the genome of the genomically recoded organism and the protein is expressed in the genomically recoded organism. The recombinant protein can then be purified. Stability or activity can then be determined by biochemical assays.

Embodiments of the present disclosure are directed to a method of making a polypeptide including at least one covalent bond between a pair of reactive side chains of corresponding amino acids, wherein the covalent bond is insensitive to reduction including genetically modifying a genomically recoded organism to express a corresponding synthetase, tRNA or synthetase/tRNA pair for translating mRNA encoding the corresponding amino acids having the reactive side chains into the polypeptide and to express the polypeptide including the at least one pair of the reactive side chains wherein the reactive side chains are oriented near one another when the expressed polypeptide is in a folded configuration, wherein the reactive side chains react to form the covalent bond that is insensitive to reduction. According to one aspect, a corresponding amino acid is selenocysteine. According to one aspect, the corresponding amino acids are selenocysteine. According to one aspect, a corresponding amino acid is cysteine. According to one aspect, the corresponding amino acids are cysteine. According to one aspect, the polypeptide further includes optimized amino acids which maintain the backbone orientation of the polypeptide when the at least one pair of reactive side chains react to form a covalent bond in the absence of a catalyst. According to one aspect, the pair of the reactive side chains on amino acids in a free form within the genomically recoded organism are unreactive in the absence of a catalyst. According to one aspect, the pair of reactive side chains include —SeH/—SeH. According to one aspect, the pair of reactive side chains include —SeH/—SH. According to one aspect, the pair of reactive side chains include selenol/selenol. According to one aspect, the pair of reactive side chains include selenol/thiol, selenol/vinyl, tetrazine/strained alkene, or boronate/saccharide. According to one aspect, the genomically recoded organism is a bacterium. According to one aspect, the genomically recoded organism is *E. coli*. According to one aspect, the covalent bond is formed in the absence of a separate catalyst.

Embodiments of the present disclosure are directed to a method of in silico polypeptide design including identifying a three-dimensional folded structure of a target polypeptide in a native environment, analyzing the three-dimensional folded structure to identify target amino acid pair geometries to accommodate geometry of at least one covalent bond between a pair of reactive side chains of corresponding amino acids, wherein the covalent bond is insensitive to reduction while substantially maintaining the three-dimensional folded structure of the target polypeptide in a native environment, substituting in silico the target amino acid pair with the pair of corresponding amino acids having the pair of reactive side chains to create a modified target polypeptide, determining a difference in geometry between the three-dimensional folded structure of the target polypeptide and a three-dimensional folded structure of the modified target polypeptide, and substituting or altering in silico neighboring native amino acids with substitute amino acids to reduce the difference between the geometry of the three-dimensional folded structure of the target polypeptide and the three-dimensional folded structure of the modified target polypeptide. According to one aspect, a corresponding amino acid is selenocysteine. According to one aspect, the corresponding amino acids are selenocysteine. According to one aspect, a corresponding amino acid is cysteine. According to one aspect, the corresponding amino acids are cysteine. According to one aspect, the pair of reactive side chains include —SeH/—SeH. According to one aspect, the pair of reactive side chains include —SeH/—SH. According to one aspect, the pair of reactive side chains include selenol/selenol. According to one aspect, the pair of reactive side chains include selenol/thiol, selenol/vinyl, tetrazine/strained alkene, or boronate/saccharide.

Embodiments of the present disclosure are directed to a method of in silico polypeptide design including computer modeling of a three-dimensional folded structure of a target polypeptide in a native environment, analyzing the three-dimensional folded structure to identify pairs of native amino acids whose positions in the structure can accommodate the geometries of at least one covalent bond between a pair of reactive side chains of corresponding amino acids, wherein the covalent bond is insensitive to reduction, while substantially maintaining the three-dimensional folded structure of the target polypeptide as in a native environment, substituting in silico the native amino acid pair with the pair of corresponding amino acids having the pair of reactive side chains to create a modified target polypeptide, determining a difference in geometry between the three-dimensional folded structure of the target polypeptide and a three-dimensional folded structure of the modified target polypeptide, and substituting or altering in silico neighboring native amino acids with other amino acids to reduce the difference between the geometry of the three-dimensional folded structure of the target polypeptide and the three-dimensional folded structure of the modified target polypeptide. According to one aspect, a corresponding amino acid is selenocysteine. According to one aspect, the corresponding amino acids are selenocysteine. According to one aspect, a corresponding amino acid is cysteine. According to one aspect, the corresponding amino acids are cysteine. According to one aspect, the pair of reactive side chains include —SeH/—SeH. According to one aspect, the pair of reactive side chains include —SeH/—SH. According to one aspect, the pair of reactive side chains include selenol/selenol. According to one aspect, the pair of reactive side chains include selenol/thiol, selenol/vinyl, tetrazine/strained alkene, or boronate/saccharide.

Embodiments of the present disclosure are directed to a method of in silico polypeptide design including computer modeling of a three-dimensional folded structure of a target polypeptide wherein the target polypeptide has an activity, analyzing the three-dimensional folded structure to identify pairs of native amino acids whose positions in the structure are candidates to accommodate the geometries of at least one covalent bond between a pair of reactive side chains of corresponding amino acids, wherein the covalent bond is insensitive to reduction, substituting in silico the native amino acid pair with the pair of corresponding amino acids having the pair of reactive side chains to create a modified target polypeptide, bonding in silico the pair of reactive side chains, and substituting in silico neighboring native amino acids with other different native amino acids or altering neighboring native amino acids to create a three-dimensional folded structure of the modified target polypeptide which is substantially similar to the three-dimensional folded structure of the target polypeptide such that the modified target polypeptide has an activity substantially similar to the target polypeptide. According to one aspect, a corresponding amino acid is selenocysteine. According to one aspect, the corresponding amino acids are selenocysteine. According to one aspect, a corresponding amino acid is cysteine. According to one aspect, the corresponding amino acids are cysteine. According to one aspect, the pair of reactive side chains include —SeH/—SeH. According to one aspect, the pair of reactive side chains include —SeH/—SH. According to one aspect, the pair of reactive side chains include selenol/selenol. According to one aspect, the pair of reactive side chains include selenol/thiol, selenol/vinyl, tetrazine/strained alkene, or boronate/saccharide.

Embodiments of the present disclosure are directed to a method of in silico polypeptide design including computer modeling of a three-dimensional folded structure of a target polypeptide with a native composition, analyzing the three-dimensional folded structure to identify pairs of native amino acids whose positions in the structure can accommodate at least one covalent bond between a pair of reactive side chains of corresponding amino acids, wherein the covalent bond is insensitive to reduction, while substantially maintaining the three-dimensional folded structure of the target polypeptide as with the native composition, substituting in silico the native amino acid pair with the pair of corresponding amino acids having the pair of reactive side chains to create a modified target polypeptide, determining a difference between the three-dimensional folded structure of the target polypeptide and a three-dimensional folded structure of the modified target polypeptide, and substituting or altering in silico neighboring native amino acids with other amino acids or other native amino acid conformations to reduce the difference between the three-dimensional folded structure of the target polypeptide and the three-dimensional folded structure of the modified target polypeptide. According to one aspect, a corresponding amino acid is selenocysteine. According to one aspect, the corresponding amino acids are selenocysteine. According to one aspect, a corresponding amino acid is cysteine. According to one aspect, the corresponding amino acids are cysteine. According to one aspect, the pair of reactive side chains include —SeH/—SeH. According to one aspect, the pair of reactive side chains include —SeH/—SH. According to one aspect, the pair of reactive side chains include selenol/selenol. According to one aspect, the pair of reactive side chains include selenol/thiol, selenol/vinyl, tetrazine/strained alkene, or boronate/saccharide.

Embodiments of the present disclosure are directed to a method of making a polypeptide including at least one covalent bond between a pair of functional groups that can react with each other when placed within the three-dimensional structure of a folded protein, wherein the covalent bond is insensitive to reduction including genetically modifying a genomically recoded organism to express a corresponding synthetase, tRNA or synthetase/tRNA pair for translating mRNA encoding corresponding amino acids having the functional groups into the polypeptide and to express the polypeptide including the functional groups wherein the functional groups are oriented near one another when the expressed polypeptide is in a folded configuration, wherein the functional groups react to form the covalent bond that is insensitive to reduction. According to one aspect, a corresponding amino acid is selenocysteine. According to one aspect, the corresponding amino acids are selenocysteine.

According to one aspect, a corresponding amino acid is cysteine. According to one aspect, the corresponding amino acids are cysteine. According to one aspect, the pair of reactive side chains include —SeH/—SeH. According to one aspect, the pair of reactive side chains include —SeH/—SH. According to one aspect, the pair of reactive side chains include selenol/selenol. According to one aspect, the pair of reactive side chains include selenol/thiol, selenol/vinyl, tetrazine/strained alkene, or boronate/saccharide.

Embodiments of the present disclosure are directed to a method of making a polypeptide including at least one pair of nonstandard amino acids with catalytically reactive side chains including genetically modifying a genomically recoded organism to express the polypeptide including at least one pair of nonstandard amino acids wherein the at least one pair of nonstandard amino acids are oriented near one another when the expressed polypeptide is in a folded configuration, and wherein the at least one pair of nonstandard amino acids react to form a covalent bond. According to one aspect, the polypeptide further includes optimized amino acids which maintain the backbone orientation of the polypeptide when the at least one pair of nonstandard amino acids react to form a covalent bond in the absence of a catalyst. According to one aspect, the at least one pair of nonstandard amino acids in a free form within the genomically recoded organism are unreactive in the absence of a catalyst. According to one aspect, the at least one pair of nonstandard amino acids includes a side chain pair selected from the group consisting of azido/aliphatic alkyne, azido/strained alkyne, ketone/amine, aldehyde/amine, ketone/hydrazide, ketone/aminooxy, aldehyde/hydrazide, aldehyde/aminooxy, and boronate/vicinal diol. According to one aspect, the genomically recoded organism has been genetically modified to express the at least one pair of nonstandard amino acids and a corresponding synthetase/tRNA pair for translating mRNA corresponding to the polypeptide into the polypeptide. According to one aspect, the genomically recoded organism is a bacterium. According to one aspect, the genomically recoded organism is E. coli. According to one aspect, the covalent bond is oxidation-reduction insensitive. According to one aspect, the covalent bond is formed in the absence of a separate catalyst.

Embodiments of the present disclosure are directed to a method of in silico polypeptide design including identifying a three-dimensional folded structure of a target polypeptide in a native environment, analyzing the three-dimensional folded structure to identify target amino acid pair geometries to accommodate geometry of a pair of nonstandard amino acids in a bonded state while substantially maintaining the three-dimensional folded structure of the target polypeptide in a native environment, substituting in silico the target amino acid pair with the pair of nonstandard amino acids to create a modified target polypeptide, determining a difference in geometry between the three-dimensional folded structure of the target polypeptide and a three-dimensional folded structure of the modified target polypeptide, and substituting or altering in silico neighboring native amino acids with substitute amino acids to reduce the difference between the geometry of the three-dimensional folded structure of the target polypeptide and the three-dimensional folded structure of the modified target polypeptide.

Embodiments of the present disclosure are directed to a method of in silico polypeptide design including computer modeling of a three-dimensional folded structure of a target polypeptide in a native environment, analyzing the three-dimensional folded structure to identify pairs of native amino acids whose positions in the structure can accommodate the geometries of a reactive, nonstandard amino acid pair in a bonded state, while substantially maintaining the three-dimensional folded structure of the target polypeptide as in a native environment, substituting in silico the native amino acid pair with the pair of nonstandard amino acids to create a modified target polypeptide, determining a difference in geometry between the three-dimensional folded structure of the target polypeptide and a three-dimensional folded structure of the modified target polypeptide, and substituting or altering in silico neighboring native amino acids with other amino acids to reduce the difference between the geometry of the three-dimensional folded structure of the target polypeptide and the three-dimensional folded structure of the modified target polypeptide.

Embodiments of the present disclosure are directed to a method of in silico polypeptide design including computer modeling of a three-dimensional folded structure of a target polypeptide wherein the target polypeptide has an activity, analyzing the three-dimensional folded structure to identify pairs of native amino acids whose positions in the structure are candidates to accommodate the geometries of a reactive, nonstandard amino acid pair in a bonded state, substituting in silico the native amino acid pair with the pair of nonstandard amino acids to create a modified target polypeptide, bonding in silico the pair of nonstandard amino acids, and substituting in silico neighboring native amino acids with other different native amino acids or altering neighboring native amino acids to create a three-dimensional folded structure of the modified target polypeptide which is substantially similar to the three-dimensional folded structure of the target polypeptide such that the modified target polypeptide has an activity substantially similar to the target polypeptide.

Embodiments of the present disclosure are directed to a method of in silico polypeptide design including computer modeling of a three-dimensional folded structure of a target polypeptide with a native composition, analyzing the three-dimensional folded structure to identify pairs of native amino acids whose positions in the structure can accommodate a reactive, nonstandard amino acid pair in a bonded state, while substantially maintaining the three-dimensional folded structure of the target polypeptide as with the native composition, substituting in silico the native amino acid pair with the pair of nonstandard amino acids to create a modified target polypeptide, determining a difference between the three-dimensional folded structure of the target polypeptide and a three-dimensional folded structure of the modified target polypeptide, and substituting or altering in silico neighboring native amino acids with other amino acids or other native amino acid conformations to reduce the difference between the three-dimensional folded structure of the target polypeptide and the three-dimensional folded structure of the modified target polypeptide.

The methods described above are more fully set forth in the following examples.

Example I

UAG Genomically Recoded Organism Suitable for Expressing Polypeptides with Non-Standard Amino Acids A Genomically Recoded Organism (GRO) in which the UAG codon translational function was completely removed was used to unambiguously incorporate non-standard amino acids (NSAAs) at UAG. See Lajoie, M. J. et al. Genomically recoded organisms expand biological functions. Science 342, 357-360, doi:10.1126/science.1241459 (2013) hereby incorporated by reference in its entirety. According to certain aspects, a genomically recoded organism includes two completely reassigned triplet codons to facilitate the incorporation of two non-standard amino acids (NSAAa). According to one aspect, triplet codons can be reassigned to incorporate non-standard amino acids using methods known to those of skill in then art. See Lajoie, M. J. et al. Probing the limits of genetic recoding in essential genes. *Science* 342, 361-363, doi:10.1126/science.1241460 (2013) hereby incorporated by reference in its entirety. Alternatively, quadruplet codons can be used to incorporate non-standard amino acids using methods known to those of skill in the art. See Anderson, J. C. et al. An expanded genetic code with a functional quadruplet codon. *Proc. Natl. Acad. Sci. U.S.A* 101, 7566-7571, doi:10.1073/pnas.0401517101 (2004), Neumann, H., Wang, K., Davis, L., Garcia-Alai, M. & Chin, J. W. Encoding multiple unnatural amino acids via evolution of a quadruplet-decoding ribosome. *Nature* 464, 441-444, (2010) and Chatterjee, A., Lajoie, M. J., Xiao, H., Church, G. M. & Schultz, P. G. A Bacterial Strain with a Unique Quadruplet Codon Specifying Non-native Amino Acids. *Chembiochem*, n/a-n/a, doi:10.1002/cbic.201402104 (2014) each of which are hereby incorporated by reference in their entireties. An orthogonal aminoacyl-tRNA synthetase (aaRS)/tRNA pair was developed that specifically and efficiently decodes the quadruplet UAGA codon based on the non-functional UAG triplet resulting in unambiguous incorporation of non-standard amino acids at UAGA codons producing high protein yields. Such quadruplet codons are useful in the present methods.

Over 100 NSAAs with diverse chemistries have been synthesized and co-translationally incorporated into proteins using evolved orthogonal aminoacyl-tRNA synthetase (aaRSs)/tRNA pairs. See Liu, C. C. & Schultz, P. G. Adding new chemistries to the genetic code. *An. Rev. Biochem.* 79, 413-444, doi:10.1146/annurev.biochem.052308.105824 (2010) hereby incorporated by refernece in its entirety. Non-standard amino acids have been designed based on tyrosine or pyrrolysine. According to certain embodiments, methods of the present invention utilize amino acids having fewer than 5 heavy atoms. Without wishing to be bound by scientific theory, smaller non-standard amino acids that have reactive functional groups are more readily able to replace natural amino acids in a protein without significantly disrupting the structure of the protein or with minimal disruption to the structure of the protein.

According to certain aspects, an aaRS/tRNA may be provided on a plasmid or into the genome of the genomically recoded organism. An orthogonal aaRS/tRNA pair is used to bioorthogonally incorporate NSAAs into proteins. Extensive work has been reported on developing vector-based over-expression systems to outcompete natural codon function with its reassigned function. See Wang, L., Brock, A., Herberich, B. & Schultz, P. G. Expanding the genetic code of *Escherichia coli*. Science 292, 498-500 (2001), Young, T. S., Ahmad, I., Yin, J. A. & Schultz, P. G. An enhanced system for unnatural amino acid mutagenesis in *E. coli*. Journal of Molecular Biology 395, 361-374 (2009), and Chatterjee, A., Sun, S. B., Furman, J. L., Xiao, H. & Schultz, P. G. A Versatile Platform for Single- and Multiple-Unnatural Amino Acid Mutagenesis in *Escherichia coli*. Biochemistry 52, 1828-1837, doi:10.1021/bi4000244 (2013) each of which are hereby incorporated by reference in their entireties. According to one aspect, completely abolishing natural UAG translation function accommodates far lower aaRS/tRNA function for efficient NSAA incorporation. Therefore, GRO-based NSAA incorporation can permit the use of vector- and/or genome-based aaRS/tRNA pairs. Genome-based aaRS/tRNA pairs have been used to reduce the mis-incorporation of canonical amino acids in the absence of available NSAAs (Mandell and Lajoie et al., 2014, Nature, accepted).

Since the UAG codon function has been completely reassigned in the genomically recoded organism, NSAAs can be incorporated in the genomically recoded organism without any phenotypic consequences. According to one aspect, NSAA incorporation in the genomically recoded organism involves supplementing the growth media with the non-standard amino acid and an inducer for the aaRS. Alternatively, the aaRS is expressed constitutively. The optimal NSAA concentration is titrated for a given aaRS/tRNA pair. Once the optimal concentration is determined, the desired protein can be overexpressed using any desired protein overexpression system (e.g. T7-RNAP, constitutive incorporation, or inducible expression based on IPTG/allolactose, anhydrotetracycline, arabinose, rhamnose, or other inducible systems). The protein cross-link will form automatically based on proximity-based geometric catalysis during protein folding, and the protein can be handled as any other over-expressed product.

Example II

Selection of Bioorthogonal Reactable NSAAs

The following criteria is used to select non-standard amino acid pairs having functional groups (side chains) that covalently bond when present in a folded protein. Such functional groups are referred to herein as being "reactable" to the extent that they react together when present in a folded protein. First, the candidate NSAA side chains are preferably not present in biological systems. The reaction mechanism by which the two side chains react are preferably unique within a biological context. Second, the covalent bonding reaction should not be catalytically favorable in solution. Representative covalent bonding reactions should be slow and/or exhibit a high energetic barrier to achieve the reaction intermediate. Third, the reaction should be capable of being catalyzed. Empirical evidence can be used to determine whether the reaction can be catalyzed. Fourth, the NSAA's themselves are preferably synthesizable by reasonable chemical routes with avenues for cost reduction and yield optimization, although any NSAAs are envisioned within the scope of the present disclosure. NSAA pairs that satisfy these criteria are considered bio-orthogonal.

The genomically recoded organism described above is used to evaluate bio-orthogonality of NSAA pairs exhibiting candidate side chain reactivities. Candidate side chains were considered bio-orthogonal if they did not affect growth, or lead to any other obvious phenotypes, in isolation or when both parts of a bond-forming NSAA candidate pair were used in culture together. Finally when cultured together, one candidate NSAA did not impair translation of the other cognate pair. To meet the third criteria, NSAA expression using previously evolved amino acyl synthetase/tRNA pairs was used. Synthetases charge a cognate amino acid substrate onto the cognate tRNA pair. An amino acid, a synthetase, and a tRNA form a triad that is required to make that amino acid competent for translation and addition to the nascent polypeptide chain. Amino acid/synthetase/tRNA triads are generally specific thereby preserving the fidelity of the translation of genetic code into proteins. As such, new synthetase/tRNA pairs that function specifically with each other are generated and used to add new NSAAs to the genetic code (or to evaluate the bio-orthogonality of bond-forming NSAA candidates). Alternatively, known synthetase/tRNA pairs are used to evaluate the bio-orthgonality of bond-forming NSAA candidate pairs.

First, genomically recoded organisms ("GRO") as described above were cultured in triplicate in LB-Lennox broth, across a dilution series from 1 uM to 10 mM (incl. 0 uM) NSAA in a 96-well plate. GRO growth (OD600) was kinetically monitored to quantify growth rates and reductions were measured as time to OD600=0.4 and Vmax (dODmax/dt). These experiments helped define the subtoxic concentration range of an NSAA of interest. Second, the GRO strain was transformed with an L-arabinose-inducible plasmid bearing the synthetase/tRNA that are specific for the NSAA side chain reactivity being evaluated. See Lajoie, M. J. et al. Genomically recoded organisms expand biological functions. Science 342, 357-360, doi:10.1126/science.1241459 (2013) hereby incorporated by reference in its entirety. Synthetase-transformed GROs were then transformed with an anhydro-tetracycline-inducible GFP_UAG reporter plasmid where UAG stop codons were incorporated into the GFP gene. Only GROs will read these codons as sense codons, not terminate the GFP_UAG translation, and generate NSAA-containing GFP that fluoresces. Patent translation of GFP_UAG (e.g., fluorescence) requires culture in NSAA and transformation with a plasmid bearing the proper synthetase/tRNA pair to use that NSAA. In this way, GFP fluorescence can be a quantitative metric for NSAA-containing protein translation. To optimize translation of the NSAA of interest, the GRO bearing both plasmid systems was cultured across a range of NSAA from 10 uM to 10 mM. Cultures were inoculated from NSAA-free overnight cultures of the GRO in LB-Lennox+Cm+kanamycin (Kan) (both Cm & Kan to maintain the synthetase expression and GFP_UAG reporter plasmids, respectively), into the same LB-Lennox broth media containing 34 ug/mL Cm, 10 ug/mL Kan, 0.2% L-arabinose, 5 ug/mL anhydro-tetracycline, and a dilution series of NSAA (0, 10 uM-10 mM) and cultured for 12-16 hours at 34 C with shaking at 700-900 rpm. Due to auto-fluorescence of LB-Lennox media, the cells were washed twice in phosphate-buffered saline (pH 7.2) by centrifugation at 4,000×g for 5 minutes. After the second wash, the cells were resuspended in 150 uL PBS for measurement of growth (OD600) and GFP fluorescence (excitation 388 nm, emission 510 nm) using a Biotek Synergy H1/H4 or a Molecular Devices M5 Spectrophotometer. GFP translation was normalized by OD600 as fluorescence divided by OD600 when measured (FL/OD), and optimal concentration of NSAA was FL/ODmax.

Once optimal NSAA concentration was determined, a candidate NSAA is tested to determine whether it impairs translation of the other cognate pair. The GRO was cultured for 12-16 hours in LB-Lennox broth media containing 34 ug/mL Cm, 10 ug/mL Kan, 0.2% L-arabinose, 5 ug/mL anhydro-tetracycline, and the optimal concentration of one candidate NSAA followed by addition of 0 or a dilution series (10 uM-10 mM) of the other candidate NSAA (with which the NSAA, held constant at its optimal concentration, may react in biological systems). After culture and washing as above, FL/OD was measured and plotted as a function of the NSAA being varied. Bio-orthogonal NSAA pairs will exhibit a concentration range across which FL/OD does not vary, indicating that reactivity between NSAAs is not occurring. On the other hand, reduction of fluorescence, but not OD suggests that the two NSAA are reacting together before translation, whether in solution or at any other step, thus reducing the pool of available NSAA for incorporation into proteins/GFP. Reduction of OD and bulk fluorescence (perhaps leaving FL/OD little changed) indicates general toxicity in the presence of both NSAAs. Both scenarios describe NSAA pairs that do not meet bio-orthogonal criteria.

Figure 3:
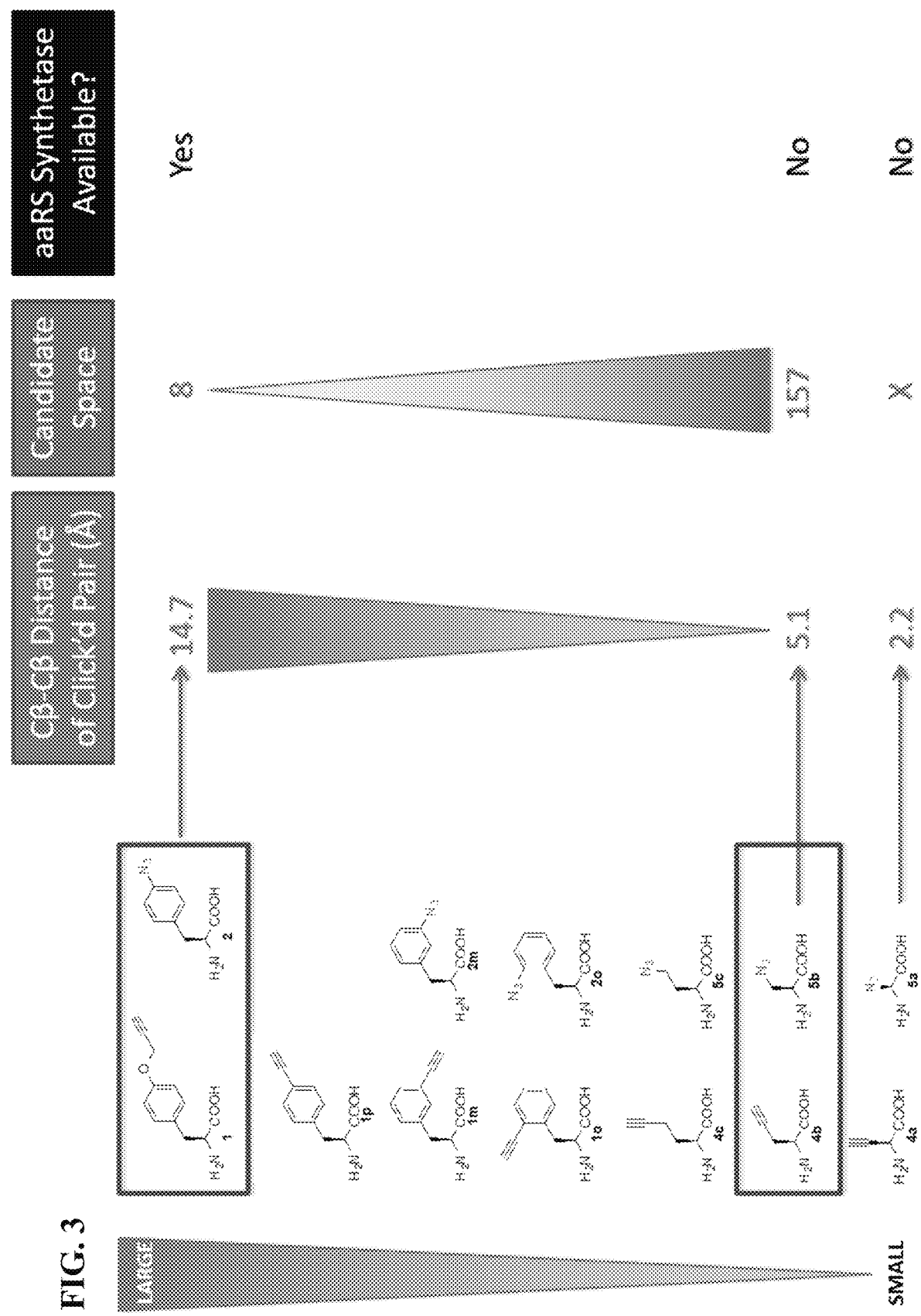
FIG. 3 shows candidate non-standard amino acid pairs having functional groups that react when present in a folded protein structure.

Aliphatic alkyne/azide pairs were selected to investigate reactive side chain pairs for bio-orthogonality. FIG. 3 shows a number of possible NSAAs that bear these reactive side chains. These two functional groups undergo a copper-catalyzed 1,3-cycloaddition to form a 5 member triazole ring, which binds together the two previously discrete linear functional groups. Without catalysis, this reaction is slow and not suitable for biological timescales, but catalysis requires conditions that are also not suitable for biological systems (high temperature, high pressure, high copper producing toxicity). Synthetase/tRNA pairs have been developed that charge aliphatic alkyne and azido derivatives of tyrosine (propargyl-oxy-phenylalanine [1] and para-azido-phenylalanine [2], pPrF and pAzF, respectively) although covalent bond formation between two proteins bearing these two NSAAs has not been demonstrated without the use of a toxic Cu[II] catalyst. See Neumann, H., Wang, K., Davis, L., Garcia-Alai, M. & Chin, J. W. Encoding multiple unnatural amino acids via evolution of a quadruplet-decoding ribosome. Nature 464, 441-444, doi:10.1038/nature08817 (2010) hereby incorporated by reference in its entirety. The distance (in Angstroms) between beta carbon of pPrF and beta carbon in pAzF in the bound state was measured computationally at 14.7 Å. Smaller NSAAs bearing these same functional groups offer the potential to reduce this adduct size, and are accommodated many more places in proteins whose structures support the geometry of the NSAAs and their covalent linkage.

Figure 4:
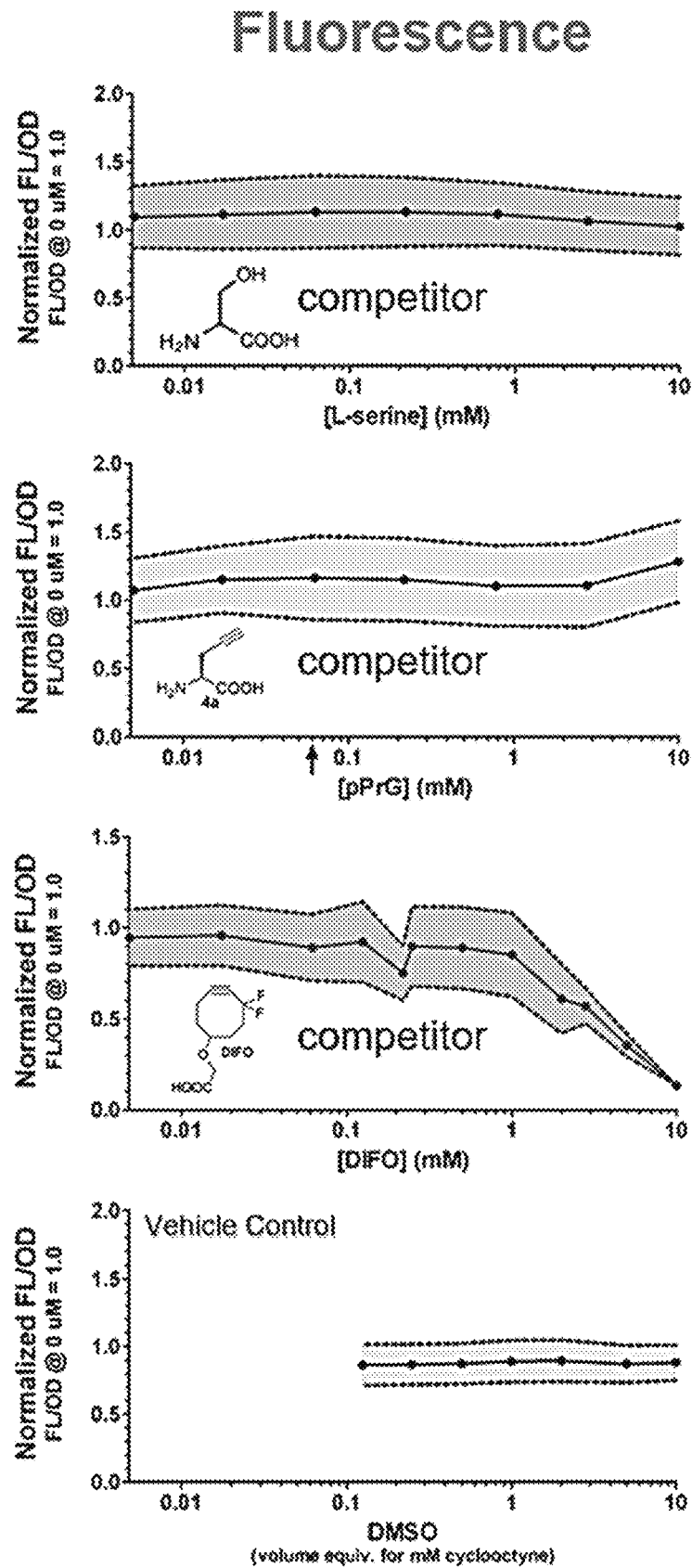
FIG. 4 shows graphical results of fluorescence and viability experiments.
Figure 4:
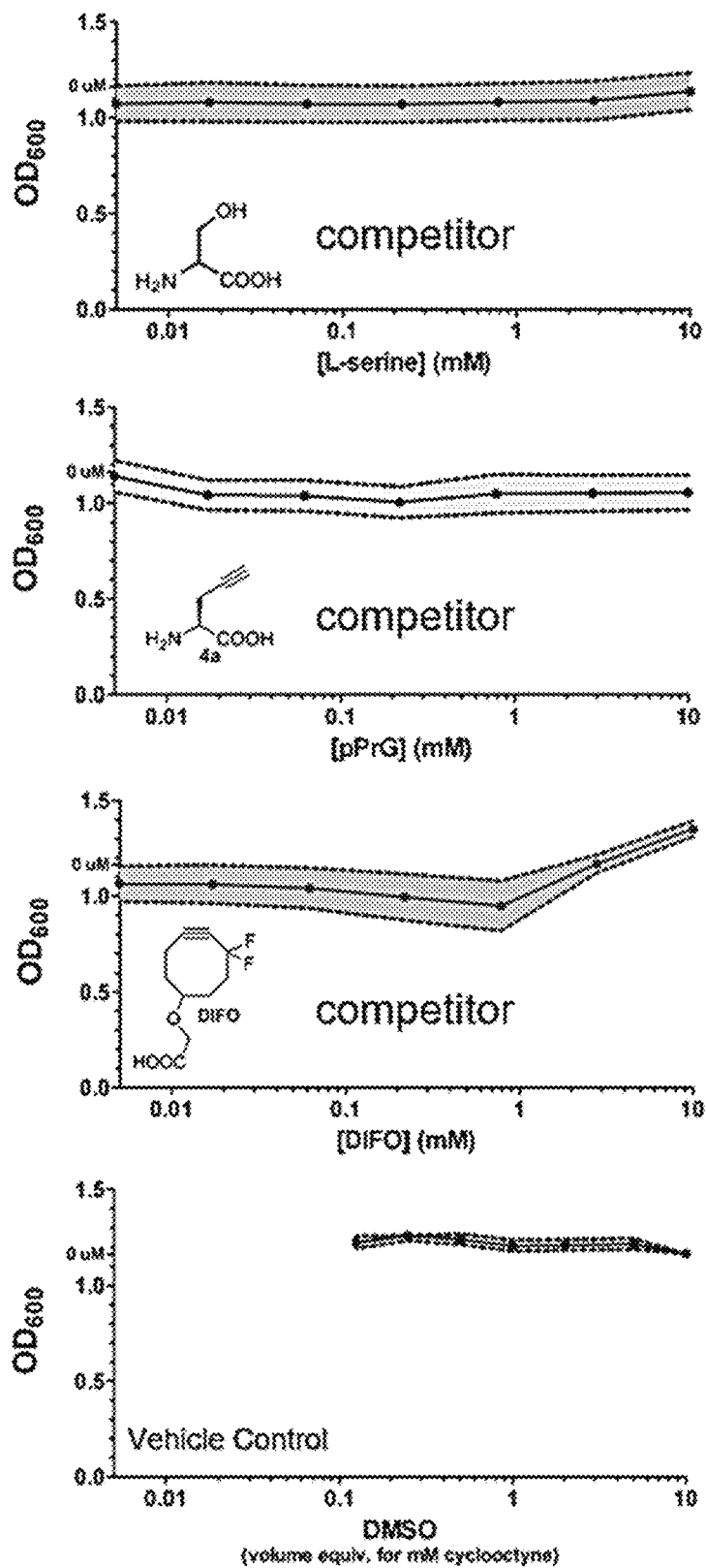

These systems were used to measure bio-orthogonality. After the optimal concentration for pPrF and pAzF in the GRO was determined, pAzF [2] was held constant at its optimum (1 mM) and alkyne containing compounds were varied from 10 uM-10 mM. In addition to co-culturing with cognate NSAA pair (compound 1 in FIG. 3), other aliphatic and cyclo-octynes were used as reagents in the competition assay. These included the aliphatic alkyne propargyl-oxyglycine (pPrG, compound 5b in FIG. 3), an unsubstituted cyclo-ocytne, a mono-fluorinated cyclooctyne (MOFO), and a difluorinated cyclo-octyne reagent (DIFO). These reagents span 4 orders of magnitude in their reactivity towards azides with pPrG being the least reactive, all cyclooctyne derivatives being more reactive than aliphatics, and fluorinated cyclooctynes exhibiting more reactivity still than unsubstituted cyclo-octynes. The pPrG and unsubstituted cyclo-octynes exhibit no reductions in FL/OD from 10 uM to 10 mM. However, more reactive fluorinated cyclooctynes exhibit toxicity (MOFO, not shown) and reductions in FL/OD at high concentrations (DIFO, FIG. 4, pink trace), consistent with undesired reactivity with pAzF. As controls, canonical amino acids with similar structures (serine, similar to pPrG, and tyrosine, similar to pPrF) do not show any reductions in OD that are consistent with reaction with pAzF, showing the specificity of this readout. By this assay, aliphatic alkynes and unsubstituted linear alkynes are shown to be bio-orthogonal with azides in vivo.

Example III

Evolution of Aminoacyl-tRNA Synthetases to Charge Reactable NSAAs

Aminoacyl-tRNA synthetases are developed to charge non-standard amino acids. Such aminoacyl-tRNA synthetases may be evolved from natural starting points. See Young, T. S. & Schultz, P. G. Beyond the canonical 20 amino acids: expanding the genetic lexicon. *J Biol Chem* 285, 11039-11044, doi:10.1074/jbc.R109.091306 (2010) hereby incorporated by reference in its entirety. Evolutionary strategies involve mutating amino acids in the natural enzyme to adjust the specificity of the enzyme from natural substrates towards synthetic NSAA substrates. New synthetases have been evolved from tyrosyl and pyrrolysyl amino acid tRNA synthetases that charge large, bulky NSAAs, usually with aromatic rings.

To evolve synthetases that charge smaller, linear NSAAs, a number of synthetase starting points that charge the most similar canonical amino acid substrates, leucine and methionine are selected. The X-ray structures of available leucine and methionine synthetases were visually inspected to determine positions to diversify. This diversity was encoded in degenerate DNA oligos that were assembled into libraries of >$10^9$ sequences. Libraries were electro-transformed into the GRO. The resulting transformants are subjected to a variety of evolutionary selections to produce highly specific synthetases for propargylglycine and azidoalanine (4a and 5b in FIG. 3, respectively).

Example IV

Quantum Mechanical Modeling of 1,3-Dipolar Cycloaddition Click Products

Reactable NSAAs are modeled in silico before suitable protein geometric catalysts can be identified discovered. Fully reacted 1,3-dipolar cycloaddition click products for all side chains were modeled with high-level quantum mechanics as covalent linkages between reactable dipeptides using Hartree-Fock calculations with a 6-31G(d) basis set. The optimized conformations were then divided into 3 entities:
1. The azide side-chain of the reacted conformation
2. The alkyne side-chain of the reacted conformation
3. The triazole ring of the reacted conformation (consisting of the 3 terminal azide nitrogens and 2 terminal alkyne carbons).

Energetically favorable conformations of (1) and (2) ("rotamers") were obtained by sampling and evaluating side chain torsions (chi angles) of each side chain within a dipeptide context and storing the conformations predicted to be energetically most favorable as rotamer libraires using the Rosetta software package for macromolecular modeling. See Renfrew, P. D., Choi, E. J., Bonneau, R. & Kuhlman, B. Incorporation of noncanonical amino acids into Rosetta and use in computational protein-peptide interface design. *PLoS One* 7, e32637, doi:10.1371/journal.pone.0032637 (2012) hereby incorporated by refernece in its entirety. The triazole ring (3) was encoded as a small molecule for geometric matching.

Example V

In Silico Modeling of Reacted Products into Protein Scaffolds

Figure 5:
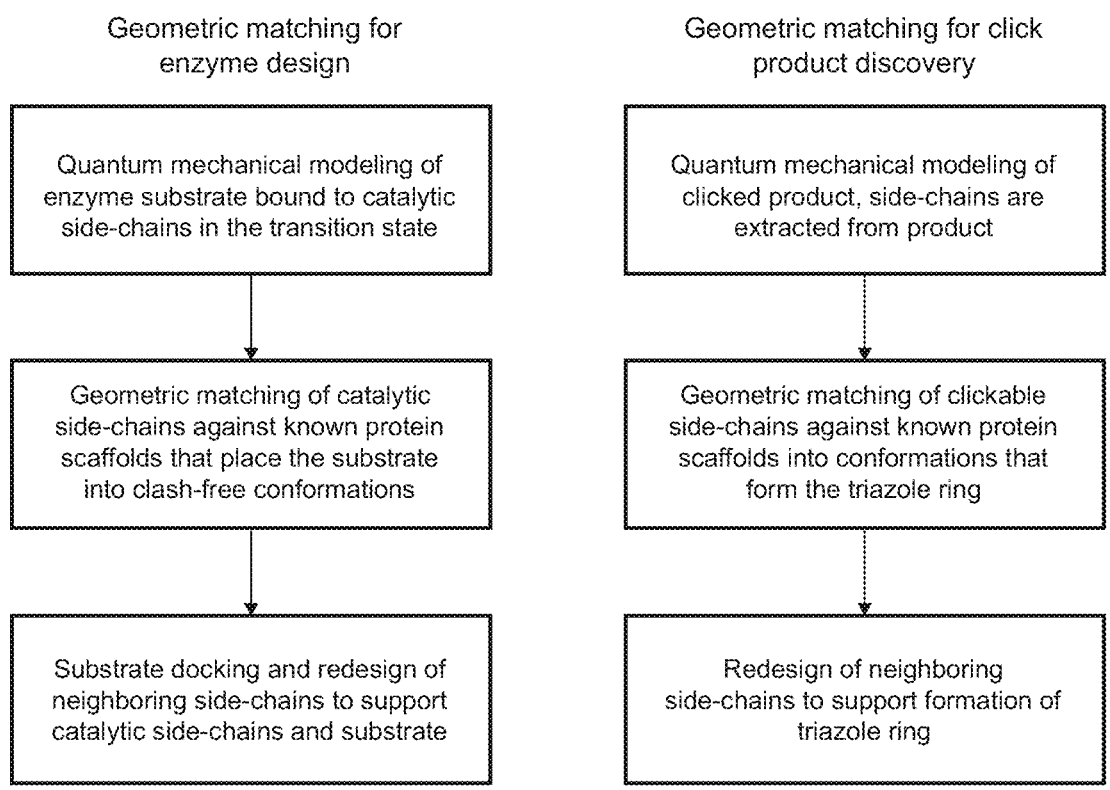
FIG. 5 shows a flow chart comparing methods of geometric matching for enzyme design and for identification of potential geometric catalysts.

Protein scaffolds capable of geometric catalysis of the 1,3-dipolar cycloaddition may be identified using a geometric matching strategy similar to the Rosetta enzyme design methodology. See Zanghellini, A. et al. New algorithms and an in silico benchmark for computational enzyme design. *Protein Sci* 15, 2785-2794, doi:10.1110/ps.062353106 (2006) hereby incorporated by reference in its entirety. The main difference is that rather than searching for protein scaffolds that accommodate the transition state complex between catalytic side-chains and an enzyme substrate, positions are sought that accommodate conformations of the azide and alkyne side-chains forming the triazole product. Differences between enzyme design and bio-orthogonal NSAA reaction product discovery are summarized in FIG. 5. Alternatively, amino acid positions suitable to accommodate the reacted product can be found by protein design simulations using Monte Carlo sampling or dead-end elimination. In all cases, these procedures can be applied to protein monomers or across polypeptide chains in complexes.

Candidates for geometric catalysis are then further refined by fixed (see Kuhlman, B. & Baker, D. Native protein sequences are close to optimal for their structures. Proc Natl Acad Sci USA 97, 10383-10388 (2000) hereby incorporated by reference in its entirety) or flexible (see Huang, P. S. et al. RosettaRemodel: a generalized framework for flexible backbone protein design. *PLoS One* 6, e24109, doi:10.1371/journal.pone.0024109 (2011) hereby incorporated by reference in its entirety) backbone protein design to improve predicted efficiency of click product formation. Designs are encoded episomally or chromosomally within GROs bearing translational machinery to produce the NSAA containing proteins, and may be purified and characterized by standard biochemical techniques, including affinity column purification, gel electrophoresis and circular dichroism.

Figure 6:
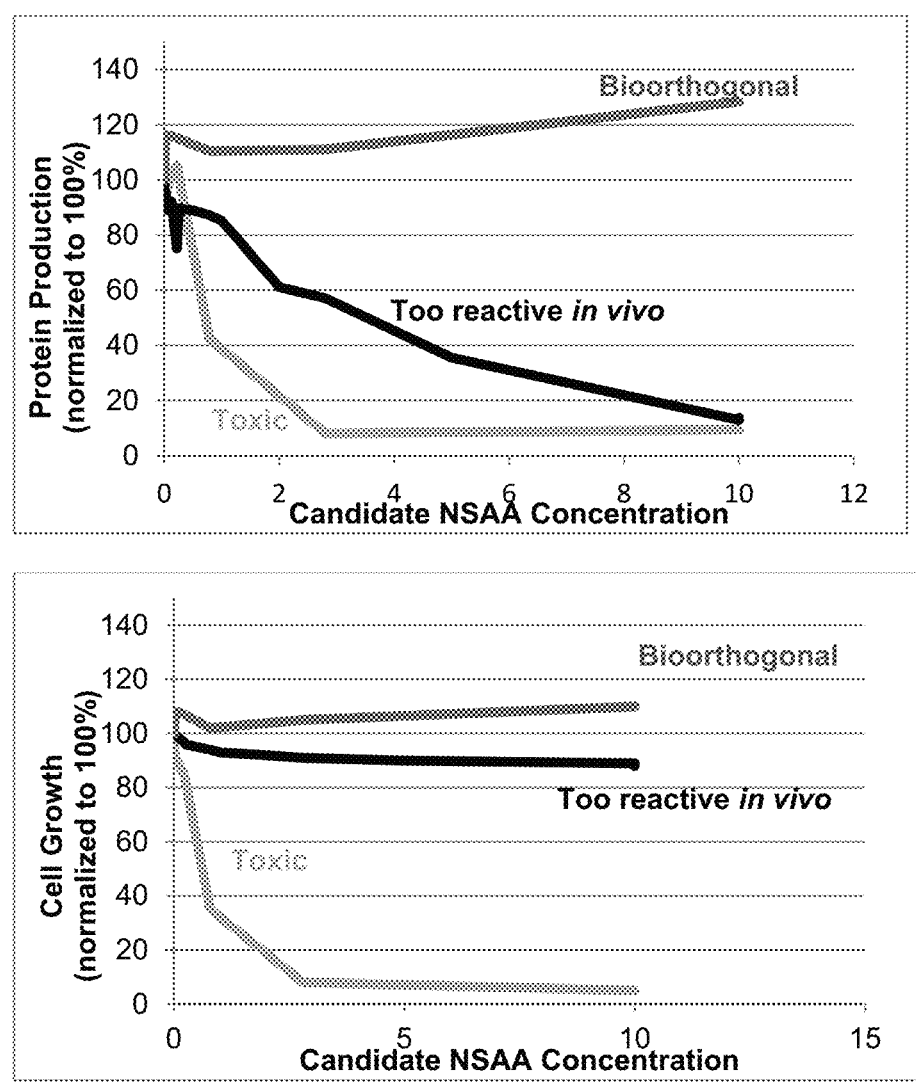
FIG. 6 shows graphs exemplifying assessment of bioorthogonality of candidate non-standard amino acids.

FIG. 6 depicts graphs exemplary of methods of assessing the bio-orthogonality of candidate non-standard amino acids with living cells. Exemplary candidate non-standard amino acids do not react with cellular compounds before they are integrated into macromolecules, and they are not toxic to the cell. Assays are used to test for bioorthogonality to determine how candidate NSAAs affect protein production and cell growth in living *E. coli*. "Bioorthogonal" NSAAs (bioorthogonal curve) will not interfere with protein production and cell growth. Alternatively, the candidate NSAA can be toxic (toxic curve) which is determined by loss of cell growth and/or protein production. Additionally, the candidate NSAA may not be bioorthogonal by being too reactive in vivo in the free form before being incorporated into a macromolecule (too reactive in vivo line), or otherwise associating with other cellular compounds to specifically impair protein production without impairing growth. Candidates that specifically impair protein production are too reactive in vivo.

Example VI

Utilities

According to certain aspects of the present disclosure, proteins engineered with the non-standard amino acids that form redox-insensitive covalent bonds have application in making proteins with improved shelf-life such as proteins that can survive transport without cooling or proteins with long-lasting shelf life at room temperature. Useful modified proteins include hyper-thermostabilized proteins that operate at high temperature intracellularly (such as isoprenoid production) or extracellularly (carbon capture enzymes, cellulases). Useful modified proteins include proteins with improved solvent tolerance (such as pH, ionic strength, denaturing cofactors, proteases, metal composition, variations in hydrophobicity and the like.)

Useful modified proteins also include stabilized antibodies as therapeutics and biosensors. According to certain aspects, the methods describe herein are used to produce redox-insensitive antibody scaffolds for use in intracellular or reducing environments as signaling proteins, biosensors, or therapeutics. Stabilized antibodies are also produced for in vivo but extracellular signaling proteins, biosensors, or therapeutics. Stabilized antibodies are also produced for ex vivo biosensors. Stabilized antibody scaffolds are also produced for optimizing antigen-binding affinities. For example, a single hyper-stabilized antibody scaffold may be used to find tight (i.e., picomolar) binders for numerous antigens.

According to an additional aspect, modified proteins including non-standard amino acids which covalently bind together are useful in designing oligomerization states. Enzymatic pathways can be designed where enzymes in sequential reactions are fixed in close proximity using a scaffold to improve transfer of products. Existing protein complexes can be covalently stabilized and covalent interactions can be engineered between different components of the enzymatic pathway.

According to an additional aspect, modified proteins including non-standard amino acids which covalently bind together are useful to switching between states of conformationally variable proteins. Enzymes can be locked into active conformations. Signaling proteins can be constitutively switched into on or off states. Flexible protein interfaces can be pre-organized to improve affinities and specificities of protein complexes.

According to an additional aspect, modified proteins including non-standard amino acids which covalently bind together are useful to design oligomerization states for protein complexes and fibrous materials. Bonds can be formed intramolecularly to rigidify oligomerized monomers, or intermolecularly to improve/titrate fiber tensile strength and elasticity. Linkages can be established in vivo or ex vivo. Ex vivo polymerization is useful for polymer production at commercially relevant scales.

According to an additional aspect, modified proteins including non-standard amino acids which covalently bind together are useful to produce high efficiency catalysis, high affinity interactions, and new protein topologies. The methods include stabilizing the native fold of enzymes permitting optimization of catalytic efficiency. The methods include driving signaling or transcriptional pathways by integrating an inter-protein bond into interaction domains. The methods include engineering covalent linkages to stabilize designed protein folds to produce new structures and function. Accordingly, methods described herein do not require a known protein with a known function. Methods described herein include de novo protein design by strategically locating non-standard amino acid pairs with reactive functional groups to produce covalent binds within a folded polypeptide.

The invention claimed is:

1. A method of in silico polypeptide design comprising
identifying a target polypeptide by using a geometric matching algorithm to scan a database of folded wild type protein structures for backbone conformations having target amino acid pair geometries to accommodate geometry of at least one covalent bond between a pair of reactive side chains of corresponding amino acids while substantially maintaining the three-dimensional folded structure of the target polypeptide, substituting in silico the target amino acid pair with the pair of corresponding amino acids having the pair of reactive side chains to create a modified target polypeptide, determining a difference in geometry between the three-dimensional folded structure of the target polypeptide and a three-dimensional folded structure of the modified target polypeptide using a geometric matching algorithm or protein design simulation, and substituting or altering in silico neighboring native amino acids or other native amino acid conformations with substitute amino acids to reduce the difference between the geometry of the three-dimensional folded structure of the target polypeptide and the three-dimensional folded structure of the modified target polypeptide, so as to optimize a reaction distance and orientation to allow the pair of reactive side chains to react under protein folding.

2. The method of claim 1 wherein the corresponding amino acids are selenocysteine.

3. The method of claim 1 wherein the corresponding amino acids are cysteine.

4. The method of claim 1 wherein the pair of reactive side chains include —SeH/—SeH.

5. The method of claim 1 wherein the pair of reactive side chains include —SeH/—SH.

6. The method of claim 1 wherein the pair of reactive side chains include selenol/selenol.

7. The method of claim 1 wherein the pair of reactive side chains include selenol/thiol, selenol/vinyl, tetrazine/strained alkene, or boronate/saccharide.

8. The method of claim 1 further comprising
computer modeling of the three-dimensional folded structure of the target polypeptide in the native environment.

9. The method of claim 1 wherein the target polypeptide has an activity.

10. The method of claim 1 wherein the identified target amino acid pair is replaced by a pair of non-standard amino acids.

11. The method of claim 1 wherein the step of analyzing the three-dimensional folded structure of the target polypeptide to identify target amino acid pair geometries to accommodate geometry of at least one covalent bond between a pair of reactive side chains of corresponding amino acids comprises identifying the target amino acid pair geometries that accommodate geometric conformations of azide and alkyne side-chains forming a triazole ring.

* * * * *